US008636667B2

(12) United States Patent
Ochs et al.

(10) Patent No.: US 8,636,667 B2
(45) Date of Patent: Jan. 28, 2014

(54) SYSTEMS AND METHODS FOR PROCESSING PHYSIOLOGICAL SIGNALS IN WAVELET SPACE

(75) Inventors: James P. Ochs, Seattle, WA (US); Paul Stanley Addison, Edinburgh (GB); James Nicholas Watson, Dunfermline (GB)

(73) Assignee: Nellcor Puritan Bennett Ireland, Mervue, Galway (*) Notice: Subject to any disclaimer, the term of this patent is extended or adjusted under 35 U.S.C. 154(b) by 1176 days.

(21) Appl. No.: 12/497,822

(22) Filed: Jul. 6, 2009

(65) Prior Publication Data
US 2011/0004069 A1 Jan. 6, 2011

(51) Int. Cl.
A61B 5/02 (2006.01)
A61B 5/024 (2006.01)
A61B 5/1455 (2006.01)

(52) U.S. Cl.
USPC ............................ 600/500; 600/481; 600/323

(58) Field of Classification Search
USPC ................. 600/310, 323, 324, 336, 344, 481, 600/500–507
See application file for complete search history.

(56) References Cited

U.S. PATENT DOCUMENTS

| 4,289,141 A | 9/1981 | Cormier |
| 4,759,369 A | 7/1988 | Taylor |
| 4,802,486 A | 2/1989 | Goodman et al. |
| 4,807,630 A | 2/1989 | Malinouskas |
| 4,859,057 A | 8/1989 | Taylor et al. |
| 4,863,265 A | 9/1989 | Flower et al. |
| 4,869,254 A | 9/1989 | Stone et al. |
| 4,911,167 A | 3/1990 | Corenman et al. |
| 4,928,692 A | 5/1990 | Goodman et al. |
| 4,934,372 A | 6/1990 | Corenman et al. |
| 4,955,379 A | 9/1990 | Hall |
| 5,078,136 A | 1/1992 | Stone et al. |
| 5,143,078 A | 9/1992 | Mather et al. |
| 5,193,543 A | 3/1993 | Yelderman |
| 5,273,036 A | 12/1993 | Kronberg et al. |

(Continued)

FOREIGN PATENT DOCUMENTS

| DE | 4210102 | 9/1993 |
| EP | 352923 | 1/1990 |

(Continued)

OTHER PUBLICATIONS

Addison, Paul S., The Illustrated Wavelet Transform Handbook, Taylor & Francis Group, 2002.

(Continued)

*Primary Examiner* — Patricia Mallari
*Assistant Examiner* — Michael Catina

(57) ABSTRACT

Methods and systems are disclosed for analyzing multiple scale bands in the scalogram of a physiological signal in order to obtain information about a physiological process. An analysis may be performed to identify multiple scale bands that are likely to contain the information sought. Each scale band may be assessed to determine a band quality, and multiple bands may be combined based on the band quality. Information about a physiological process may determined based on the combined band. In an embodiment, analyzing multiple scale bands in a scalogram arising from a wavelet transformation of a photoplethysmograph signal may yield clinically relevant information about, among other things, the blood oxygen saturation of a patient.

20 Claims, 12 Drawing Sheets
(2 of 12 Drawing Sheet(s) Filed in Color)

(56) References Cited

U.S. PATENT DOCUMENTS

| | | | |
|---|---|---|---|
| 5,413,100 A | 5/1995 | Barthelemy et al. | |
| 5,431,159 A | 7/1995 | Baker et al. | |
| 5,439,483 A | 8/1995 | Duong-Van | |
| RE35,122 E | 12/1995 | Corenman et al. | |
| 5,482,036 A | 1/1996 | Diab et al. | |
| 5,490,505 A | 2/1996 | Diab et al. | |
| 5,494,032 A | 2/1996 | Robinson et al. | |
| 5,590,650 A | 1/1997 | Genova | |
| 5,632,272 A | 5/1997 | Diab et al. | |
| 5,676,141 A | 10/1997 | Hollub | |
| 5,685,299 A | 11/1997 | Diab et al. | |
| 5,685,301 A | 11/1997 | Klomhaus | |
| 5,743,263 A | 4/1998 | Baker, Jr. | |
| 5,769,785 A | 6/1998 | Diab et al. | |
| 5,778,881 A | 7/1998 | Sun et al. | |
| 5,795,304 A | 8/1998 | Sun et al. | |
| 5,797,840 A | 8/1998 | Akselrod et al. | |
| 5,823,950 A | 10/1998 | Diab et al. | |
| 5,827,195 A | 10/1998 | Lander | |
| 5,830,137 A | 11/1998 | Scharf | |
| 5,853,364 A | 12/1998 | Baker, Jr. | |
| 5,855,205 A | 1/1999 | Papaionnou | |
| 5,879,294 A | 3/1999 | Anderson et al. | |
| 5,967,995 A | 10/1999 | Shusterman et al. | |
| 5,971,930 A | 10/1999 | Elghazzawi | |
| 5,991,648 A | 11/1999 | Levin | |
| 6,002,952 A | 12/1999 | Diab et al. | |
| 6,022,321 A | 2/2000 | Amano et al. | |
| 6,027,453 A | 2/2000 | Miwa et al. | |
| 6,036,642 A | 3/2000 | Diab et al. | |
| 6,036,653 A * | 3/2000 | Baba et al. | 600/500 |
| 6,067,462 A | 5/2000 | Diab et al. | |
| 6,081,735 A | 6/2000 | Diab et al. | |
| 6,083,172 A | 7/2000 | Baker, Jr. | |
| 6,094,592 A | 7/2000 | Yorkey et al. | |
| 6,095,984 A | 8/2000 | Amano et al. | |
| 6,117,075 A | 9/2000 | Barnea | |
| 6,122,535 A | 9/2000 | Kaestle et al. | |
| 6,129,675 A | 10/2000 | Jay | |
| 6,135,966 A | 10/2000 | Ko | |
| 6,157,850 A | 12/2000 | Diab et al. | |
| 6,171,257 B1 | 1/2001 | Weil et al. | |
| 6,171,258 B1 | 1/2001 | Karakasoglu et al. | |
| 6,206,830 B1 | 3/2001 | Diab et al. | |
| 6,208,951 B1 | 3/2001 | Kumar et al. | |
| 6,217,523 B1 | 4/2001 | Amano et al. | |
| 6,236,872 B1 | 5/2001 | Diab et al. | |
| 6,263,222 B1 | 7/2001 | Diab et al. | |
| 6,293,915 B1 * | 9/2001 | Amano et al. | 600/501 |
| 6,325,761 B1 | 12/2001 | Jay | |
| 6,330,468 B1 | 12/2001 | Scharf | |
| 6,339,715 B1 | 1/2002 | Bahr et al. | |
| 6,361,501 B1 | 3/2002 | Amano et al. | |
| 6,363,270 B1 | 3/2002 | Colla et al. | |
| 6,393,311 B1 | 5/2002 | Edgar, Jr. et al. | |
| 6,405,069 B1 | 6/2002 | Oraevsky et al. | |
| 6,411,833 B1 | 6/2002 | Baker, Jr. | |
| 6,480,729 B2 | 11/2002 | Stone | |
| 6,501,975 B2 | 12/2002 | Diab et al. | |
| 6,519,486 B1 | 2/2003 | Edgar, Jr. et al. | |
| 6,561,986 B2 | 5/2003 | Baura et al. | |
| 6,574,491 B2 | 6/2003 | Elghazzawi | |
| 6,594,512 B2 | 7/2003 | Huang | |
| 6,608,934 B2 | 8/2003 | Scheirer et al. | |
| 6,631,281 B1 | 10/2003 | Kastle | |
| 6,647,280 B2 | 11/2003 | Bahr et al. | |
| 6,650,917 B2 | 11/2003 | Diab et al. | |
| 6,650,918 B2 | 11/2003 | Terry | |
| 6,654,623 B1 | 11/2003 | Kastle | |
| 6,658,276 B2 | 12/2003 | Kianl et al. | |
| 6,658,277 B2 | 12/2003 | Wasserman | |
| RE38,476 E | 3/2004 | Diab et al. | |
| 6,699,194 B1 | 3/2004 | Diab et al. | |
| 6,709,402 B2 | 3/2004 | Dekker | |
| RE38,492 E | 4/2004 | Diab et al. | |
| 6,721,584 B2 | 4/2004 | Baker, Jr. | |
| 6,721,585 B1 | 4/2004 | Parker | |
| 6,745,060 B2 | 6/2004 | Diab et al. | |
| 6,748,252 B2 | 6/2004 | Lynn et al. | |
| 6,780,158 B2 | 8/2004 | Yarita | |
| 6,810,277 B2 | 10/2004 | Edgar, Jr. et al. | |
| 6,826,419 B2 | 11/2004 | Diab et al. | |
| 6,836,679 B2 | 12/2004 | Baker, Jr. | |
| 6,842,635 B1 | 1/2005 | Parker | |
| 6,850,787 B2 | 2/2005 | Weber et al. | |
| 6,931,269 B2 | 8/2005 | Terry | |
| 6,961,598 B2 | 11/2005 | Diab | |
| 6,970,792 B1 | 11/2005 | Diab | |
| 7,001,337 B2 | 2/2006 | Dekker | |
| 7,020,507 B2 | 3/2006 | Scharf et al. | |
| 7,025,728 B2 | 4/2006 | Ito et al. | |
| 7,035,679 B2 | 4/2006 | Addison et al. | |
| 7,043,293 B1 | 5/2006 | Baura | |
| 7,054,453 B2 | 5/2006 | Causevic et al. | |
| 7,054,454 B2 | 5/2006 | Causevic et al. | |
| 7,072,702 B2 | 7/2006 | Edgar, Jr. et al. | |
| 7,079,888 B2 | 7/2006 | Oung et al. | |
| 7,139,599 B2 | 11/2006 | Terry | |
| 7,171,269 B1 | 1/2007 | Addison et al. | |
| 7,173,525 B2 | 2/2007 | Albert | |
| 7,194,292 B2 | 3/2007 | Norris | |
| 7,203,267 B2 | 4/2007 | De Man et al. | |
| 7,215,984 B2 | 5/2007 | Diab et al. | |
| 7,215,985 B2 | 5/2007 | Petersen et al. | |
| 7,215,986 B2 | 5/2007 | Diab et al. | |
| 7,225,013 B2 | 5/2007 | Geva et al. | |
| 7,254,433 B2 | 8/2007 | Diab et al. | |
| 7,254,500 B2 | 8/2007 | Makeig et al. | |
| 7,289,835 B2 | 10/2007 | Mansfield et al. | |
| 7,328,053 B1 | 2/2008 | Diab et al. | |
| 7,373,194 B2 | 5/2008 | Weber et al. | |
| 7,376,453 B1 | 5/2008 | Diab et al. | |
| 7,377,899 B2 | 5/2008 | Weber et al. | |
| 7,383,070 B2 | 6/2008 | Diab et al. | |
| 7,423,526 B2 | 9/2008 | Despotis | |
| 7,440,787 B2 | 10/2008 | Diab | |
| 7,515,949 B2 | 4/2009 | Norris | |
| 7,519,488 B2 | 4/2009 | Fu et al. | |
| 7,523,011 B2 | 4/2009 | Akiyama et al. | |
| 2002/0103423 A1 | 8/2002 | Chin et al. | |
| 2002/0128544 A1 | 9/2002 | Diab et al. | |
| 2003/0163057 A1 | 8/2003 | Flick et al. | |
| 2003/0220576 A1 | 11/2003 | Diab | |
| 2003/0225337 A1 | 12/2003 | Scharf et al. | |
| 2003/0236452 A1 | 12/2003 | Melker et al. | |
| 2004/0010188 A1 | 1/2004 | Wasserman | |
| 2004/0039273 A1 | 2/2004 | Terry | |
| 2004/0064020 A1 | 4/2004 | Diab et al. | |
| 2004/0068164 A1 | 4/2004 | Diab et al. | |
| 2004/0087846 A1 | 5/2004 | Wasserman | |
| 2004/0092805 A1 | 5/2004 | Yarita | |
| 2004/0138540 A1 | 7/2004 | Baker et al. | |
| 2004/0158135 A1 | 8/2004 | Baker et al. | |
| 2004/0171948 A1 | 9/2004 | Terry | |
| 2004/0181134 A1 | 9/2004 | Baker et al. | |
| 2004/0204636 A1 | 10/2004 | Diab et al. | |
| 2004/0204637 A1 | 10/2004 | Diab et al. | |
| 2004/0204638 A1 | 10/2004 | Diab et al. | |
| 2004/0210146 A1 | 10/2004 | Diab et al. | |
| 2004/0267140 A1 | 12/2004 | Ito et al. | |
| 2005/0033129 A1 | 2/2005 | Edgar et al. | |
| 2005/0043616 A1 | 2/2005 | Chinchoy | |
| 2005/0049470 A1 | 3/2005 | Terry | |
| 2005/0209517 A1 | 9/2005 | Diab et al. | |
| 2005/0267346 A1 | 12/2005 | Faber et al. | |
| 2005/0277818 A1 | 12/2005 | Myers | |
| 2006/0052680 A1 | 3/2006 | Diab | |
| 2006/0122476 A1 | 6/2006 | Van Slyke | |
| 2006/0149149 A1 | 7/2006 | Schmid | |
| 2006/0176471 A1 | 8/2006 | Hendriks | |
| 2006/0200016 A1 | 9/2006 | Diab et al. | |
| 2006/0209631 A1 | 9/2006 | Melese et al. | |
| 2006/0211930 A1 | 9/2006 | Scharf et al. | |
| 2006/0217609 A1 | 9/2006 | Diab et al. | |

(56) References Cited

U.S. PATENT DOCUMENTS

| | | |
|---|---|---|
| 2006/0229519 A1 | 10/2006 | Fujiwara et al. |
| 2006/0253010 A1 | 11/2006 | Brady et al. |
| 2006/0258921 A1* | 11/2006 | Addison et al. ............... 600/323 |
| 2006/0258927 A1 | 11/2006 | Edgar et al. |
| 2006/0265022 A1 | 11/2006 | John et al. |
| 2006/0287587 A1 | 12/2006 | Yarita |
| 2006/0287588 A1 | 12/2006 | Yarita |
| 2007/0004677 A1* | 1/2007 | Chao et al. ................ 514/64 |
| 2007/0004977 A1 | 1/2007 | Norris |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0149871 A1 | 6/2007 | Sarussi et al. |
| 2007/0167694 A1 | 7/2007 | Causevic et al. |
| 2007/0167851 A1 | 7/2007 | Vitali et al. |
| 2007/0203417 A1 | 8/2007 | Wasserman et al. |
| 2007/0208259 A1 | 9/2007 | Mannheimer |
| 2007/0213621 A1 | 9/2007 | Reisfeld et al. |
| 2007/0219059 A1 | 9/2007 | Schwartz et al. |
| 2007/0225581 A1 | 9/2007 | Diab et al. |
| 2007/0249918 A1 | 10/2007 | Diab et al. |
| 2007/0282212 A1 | 12/2007 | Sierra et al. |
| 2007/0291832 A1 | 12/2007 | Diab et al. |
| 2008/0004514 A1 | 1/2008 | Diab et al. |
| 2008/0030346 A1 | 2/2008 | Despotis |
| 2008/0033266 A1 | 2/2008 | Diab et al. |
| 2008/0036752 A1 | 2/2008 | Diab et al. |
| 2008/0045823 A1 | 2/2008 | Diab et al. |
| 2008/0045832 A1 | 2/2008 | McGrath |
| 2008/0082018 A1 | 4/2008 | Sackner et al. |
| 2008/0137066 A1 | 6/2008 | Weinstein et al. |
| 2008/0167541 A1 | 7/2008 | Takala et al. |
| 2008/0167564 A1 | 7/2008 | Hete et al. |
| 2008/0194925 A1 | 8/2008 | Alsafadi et al. |
| 2008/0200786 A1 | 8/2008 | Berndsen |
| 2008/0214903 A1 | 9/2008 | Orbach |
| 2008/0221402 A1 | 9/2008 | Despotis |
| 2008/0243021 A1 | 10/2008 | Causevic et al. |

FOREIGN PATENT DOCUMENTS

| | | |
|---|---|---|
| EP | 734221 | 10/1996 |
| EP | 734223 | 10/1996 |
| EP | 1006864 | 6/2000 |
| JP | 09084776 | 3/1997 |
| JP | 10216114 | 8/1998 |
| JP | 10337282 | 12/1998 |
| JP | 24202190 | 7/2004 |
| JP | 24248819 | 9/2004 |
| JP | 24290412 | 10/2004 |
| JP | 25253865 | 9/2005 |
| JP | 28110108 | 5/2008 |
| JP | 28188216 | 8/2008 |
| WO | WO-95/16388 | 6/1995 |
| WO | WO-98/43071 | 10/1998 |
| WO | WO-01/25802 | 4/2001 |
| WO | WO-01/62152 | 8/2001 |
| WO | WO-03/000125 | 1/2003 |
| WO | WO-03/055395 | 7/2003 |
| WO | WO-03/071939 | 9/2003 |
| WO | WO-2004/075746 | 9/2004 |
| WO | WO-2004/105601 | 12/2004 |
| WO | WO-2005/096170 | 10/2005 |
| WO | WO-2006/085120 | 8/2006 |
| WO | WO-2007/013708 | 2/2007 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR PROCESSING PHYSIOLOGICAL SIGNALS IN WAVELET SPACE

SUMMARY OF THE DISCLOSURE

The present disclosure relates to physiological signal analysis and, more particularly, the present disclosure relates to analyzing multiple scale bands in a scalogram of a physiological signal in order to obtain information about a physiological process.

Different representations of a physiological signal, generated by applying different transformation techniques, may reveal different features of the signal. A scalogram representation of a physiological signal may be generated by applying a continuous wavelet transformation, for example, and may allow useful physiological information to be derived. In order to derive such useful information (e.g., clinical information) from a scalogram, an analysis may be performed to identify one or more scale bands that are likely to contain the information sought. Often, information about a physiological process of interest is contained in a first scale band of the scalogram. For example, in the context of a plethysmograph signal, information about a patients blood oxygen saturation may be contained in a scale band associated with the patient's pulse rate. However, useful information may also be contained in additional bands. Such additional bands may be related to the first band, and may arise, for example, because of physiological phenomena such as internal reflections. Related bands may provide useful information regarding the physiological process by identifying physiologically-relevant features, improving the quality of the derived information, or a combination of the two.

In some applications, related scale bands may be associated with scales that are integer multiples of a first scale. For example, a pulse band in a scalogram may be associated with a scale corresponding to the pulse rate, and related bands may be associated with scales corresponding to twice the pulse rate scale, three times the pulse rate scale, etc. In some applications, related scale bands may be located by identifying other features within the scalogram, such as ridges or local maxima, which may occur at non-integer multiples of a first scale band.

Certain types of noise and artifact may influence certain scale bands more than others. Thus, combining related bands for the purpose of deriving information about a physiological process may allow for more consistent and accurate determination of such information than may be achievable using only a single scale band. A combination may include a weighted combination or a concatenation of data. Combining related bands may also include removing a portion or portions of signal that have undesirable characteristics, such as excess noise.

Because different scale bands may be differently influenced by noise and artifact, and may also reveal different features of the physiological process of interest, the quality of the information provided by each scale band may vary between bands and across time. Thus, it may be advantageous to assess the quality of related scale bands and use the results of the assessment in combining the bands. For example, a band whose quality is determined to be low may have a reduced influence in a combination. A band quality may be assessed in several ways, and may be based on any one or more of an energy or relative energy of a portion of the band, a measure of the consistency of the amplitude of a portion of the band, a comparison (e.g., a correlation) of multiple components of a received signal, and an evaluation in the time domain.

A combination of bands may be used to determine information regarding a physiological process reflected in the identified bands. For example, a combination of bands related to the pulse band of a plethysmograph signal may be used to determine any of a number of physical parameters, such as blood oxygen saturation. This information may be used in a variety of clinical applications, including within diagnostic and predictive models, and may be recorded and/or displayed by a patient monitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
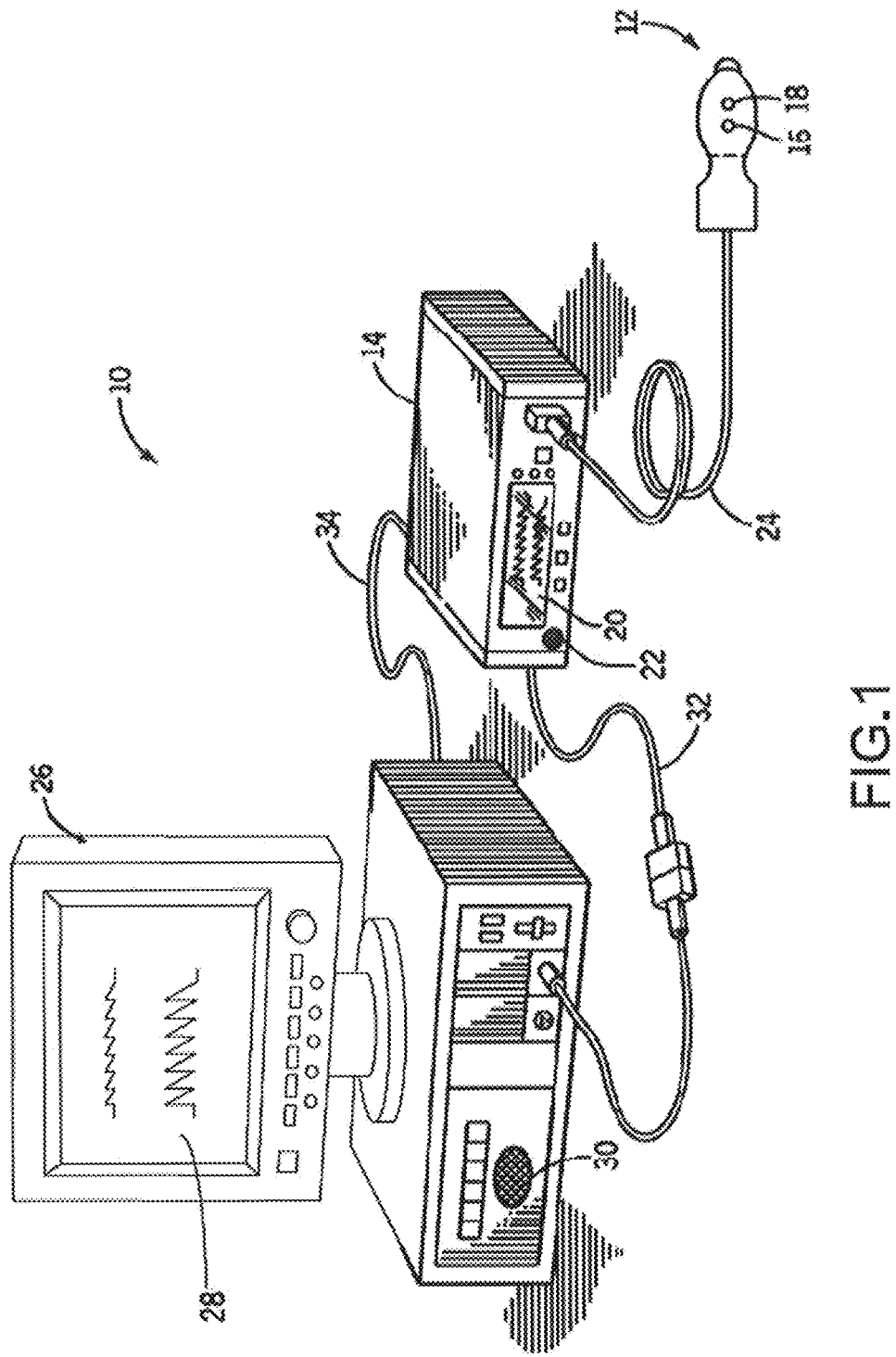
FIG. 1 shows an illustrative patient monitoring system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_0(\lambda)\exp(-(s\beta_o(\lambda)+(1-s)\beta_r(\lambda))l(t)) \tag{1}$$

where:
$\lambda$=wavelength;
t=time;
I=intensity of light detected;
$I_0$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.
1. The natural logarithm of Eq. 1 is taken ("log" will be used to represent the natural logarithm) for IR and Red to yield $$\log I = \log I_0 - (s\beta_o + (1-s)\beta_r)l. \tag{2}$$

2. Eq. 2 is then differentiated with respect to time to yield $$\frac{d\log I}{dt} = -(s\beta_o + (1-s)\beta_r)\frac{dl}{dt}. \tag{3}$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \tag{4}$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}. \tag{5}$$

5. Note that, in discrete time, the following approximation can be made:

$$\frac{d\log I(\lambda, t)}{dt} \simeq \log I(\lambda, t_2) - \log I(\lambda, t_1) \tag{6}$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \tag{7}$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R. \tag{8}$$

where R represents the "ratio of ratios."
8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \tag{9}$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \tag{10}$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \tag{11}$$

$$\frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R,$$

which defines a cluster of points whose slope of y versus x will give R when $$x = [I(t_2, \lambda_{IR}) - I(t_1, \lambda_{IR})]I(t_1, \lambda_R), \qquad (12)$$

and $$y = [I(t_2, \lambda_R) - I(t_1, \lambda_R)]I(t_1, \lambda_{IR}). \qquad (13)$$

FIG. 1 is a perspective view of an embodiment of a patient monitoring system 10. In an embodiment, system 10 is implemented as part of a pulse oximetry system. System 10 may include a sensor 12 and a monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be a charged coupled device (CCD) sensor. In another embodiment, the sensor array may be made up of a combination of CMOS and CCD sensors. A CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the effort or oximetry reading may be passed to monitor 14. Further, monitor 14 may include a display 20 configured to display a patient's physiological parameters or information about the system. In the embodiment shown, monitor 14 may also include a speaker 22 to provide an audible sound that may be used in various other embodiments, such as sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation (referred to as an "SpO$_2$" measurement) generated by monitor 14, pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively, and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
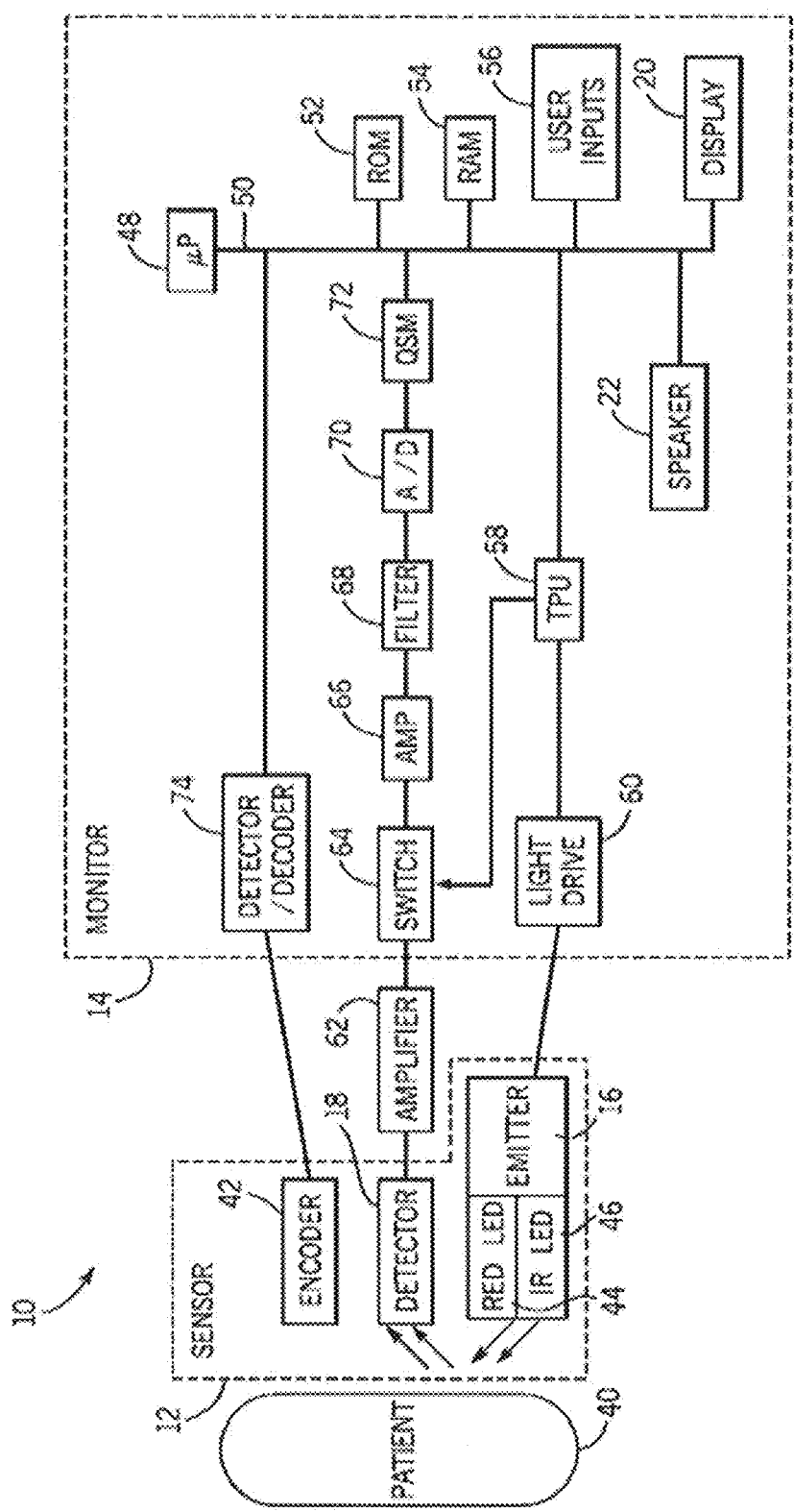
FIG. 2 is a block diagram of the illustrative patient monitoring system of FIG. 1 coupled to a patient in accordance with an embodiment.

FIG. 2 is a block diagram of a patient monitoring system, such as patient monitoring system 10 of FIG. 17 which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit one or more wavelengths of light (e.g., Red and/or IR) into a patient's tissue 40. Hence, emitter 16 may include a Red light emitting light source such as Red light emitting diode (LED) 44 and/or an IR light emitting light source such as IR LED 46 for emitting light into the patient's tissue 40 at the wavelengths used to calculate the patient's physiological parameters. In one embodiment, the Red wavelength may be between about 600 nm and about 700 nm, and the IR wavelength may be between about 800 nm and about 1000 nm. In embodiments in which a sensor array is used in place of a single sensor, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the Red LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. Such information may be stored in a suitable memory (e.g., RAM 54) and may allow monitor 14 to determine, for example, patient-specific threshold ranges in which the patient's physiological parameter measurements should fall and to enable or disable additional physiological parameter algorithms. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point at which a probe or sensor is attached.

Noise (e.g., from patient movement) can degrade a pulse oximetry signal relied upon by a physician without the physician's awareness. This is especially true if the monitoring of the patient is remote, the motion is too small to be observed, or the doctor is watching the instrument or other parts of the patient and not the sensor site. Processing physiological signals may involve operations that reduce the amount of noise present in the signals or otherwise identify noise components in order to prevent them from affecting measurements of physiological parameters derived from the physiological signals.

It will be understood that the present disclosure is applicable to any suitable signals and that PPG signals may be used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a physiological signal may be transformed using a continuous wavelet transform. Information derived from the transform of the physiological signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (14)$$

where ψ*(t) is the complex conjugate of the wavelet function ψ(t), a is the dilation parameter of the wavelet and b is the location parameter of the wavelet. The transform given by Eq. 14 may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others, may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (15)$$

where '||' is the modulus operator. The scalogram may be rescaled for useful purposes. One common rescaling is defined as $$S_R(a, b) = \frac{|T(a, b)|^2}{a} \qquad (16)$$

and is useful for defining ridges in wavelet space when, for example, the Morlet wavelet is used. Ridges are defined as a locus of points of local maxima in the plane. A ridge associated with only the locus of points of local maxima in the plane is labeled a "maxima ridge." Also included as a definition of a ridge are paths displaced from the locus of the local maxima. Any reasonable definition of a ridge may be employed in the methods described herein.

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and a multiplication of the result by $\sqrt{a}$.

In the discussion of the technology which follows herein, the term "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform T(a,b) itself or any part thereof. For example, the real part of the wavelet transform, the imaginary part of the wavelet transform, the phase of the wavelet transform, any other suitable part of the wavelet transform, or any combination thereof is intended to be conveyed by the term "scalogram."

A scale, which may be interpreted as a representative temporal period, may be converted to a characteristic frequency of the wavelet function. The characteristic frequency associated with a wavelet of arbitrary a scale is given by $$f = \frac{f_c}{a}, \quad (17)$$

where $f_c$ is the characteristic frequency of the mother wavelet (i.e., at a=1) and becomes a scaling constant, and f is the representative or characteristic frequency for the wavelet at arbitrary scale a.

Any suitable wavelet function may be used in connection with the present disclosure. One of the most commonly used complex wavelets, the Morlet wavelet, is defined as $$\psi(t) = \pi^{-1/4}(e^{i2\pi f_0 t} - e^{-(2\pi f_0)^2/2})e^{-t^2/2}, \quad (18)$$

where $f_0$ is the central frequency of the mother wavelet. The second term in the parentheses is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2}. \quad (19)$$

This wavelet is a complex wave within a scaled Gaussian envelope. While both definitions of the Morlet wavelet are included herein, the function of Eq. 19 is not strictly a wavelet as it has a non-zero mean (i.e., the zero frequency term of its corresponding energy spectrum is non-zero). However, it will be recognized by those skilled in the art that Eq. 19 may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information.

Figure 3B:
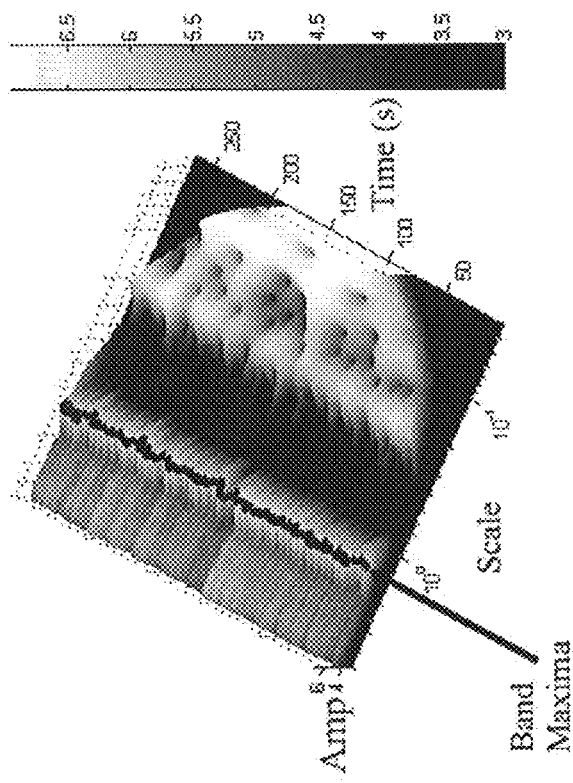
FIGS. 3(a) and 3(b) show illustrative views of a scalogram derived from a PPG signal in accordance with an embodiment.
Figure 3A:
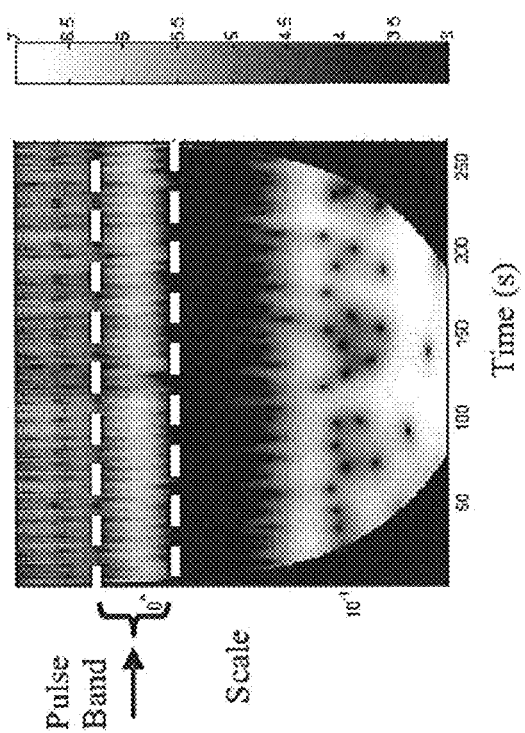

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in Eq. 16, the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
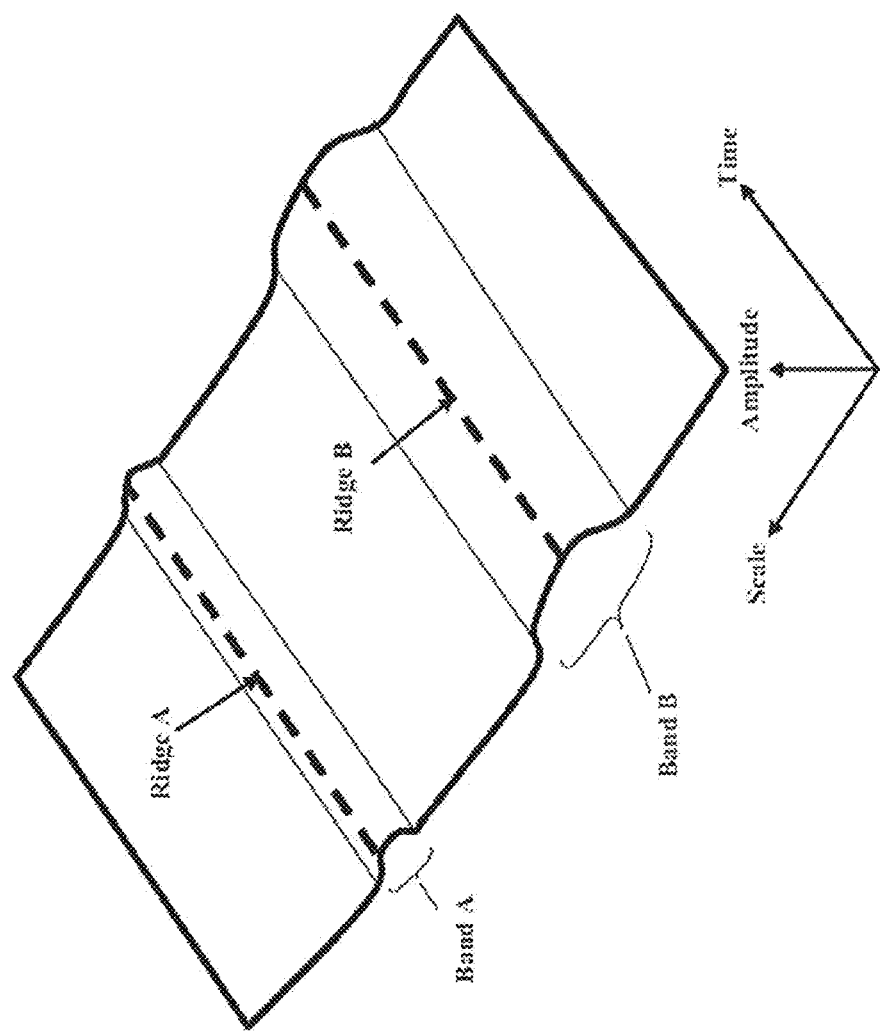
FIG. 3(c) shows an illustrative scalogram derived from a signal containing two pertinent components in accordance with an embodiment.
Figure 3D:
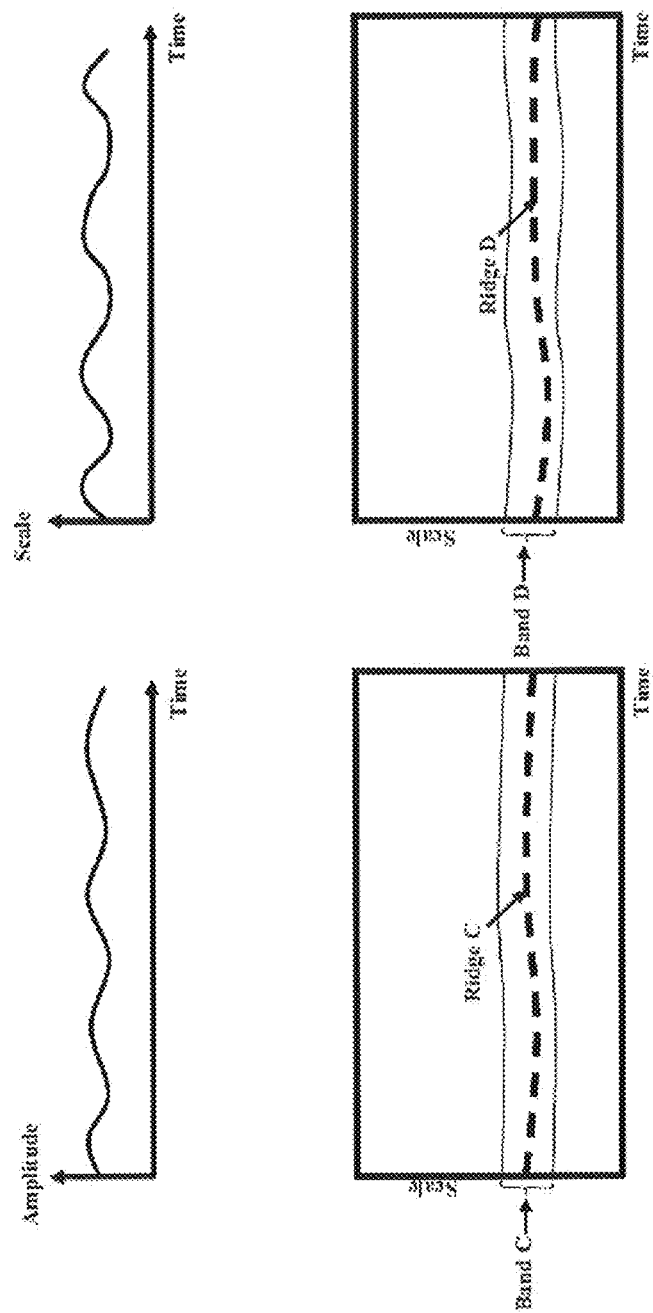
FIG. 3(d) shows an illustrative schematic of signals associated with a ridge of FIG. 3(c) and illustrative schematics of a further wavelet decomposition of derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary, and may vary in scale, amplitude, or both, over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, a band ridge is defined as the locus of the peak values of these bands with respect to scale. For purposes of discussion, it may be assumed that band B contains the signal information of interest. Band B will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B, then the information within band B can become ambiguous (i.e., obscured, fragmented or missing). In this case, the ridge of band A (referred to herein as "ridge A") may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts, remove noise, combine bands, or any combination thereof. In one embodiment, there is an inverse continuous wavelet transform which allows the original signal to be recovered from its wavelet transform by integrating over all scales and locations, a and b, in accordance with $$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2}, \quad (20)$$

which may also be written as $$x(t) = \frac{1}{C_g} \int_{-\infty}^{\infty} \int_0^{\infty} T(a,b) \psi_{a,b}(t) \frac{da\,db}{a^2}. \quad (21)$$

where $C_g$ is a scalar value known as the admissibility constant. It is wavelet-type dependent and may be calculated in accordance with $$C_g = \int_0^{\infty} \frac{|\hat{\psi}(f)|^2}{f} df. \quad (22)$$

Figure 3E:
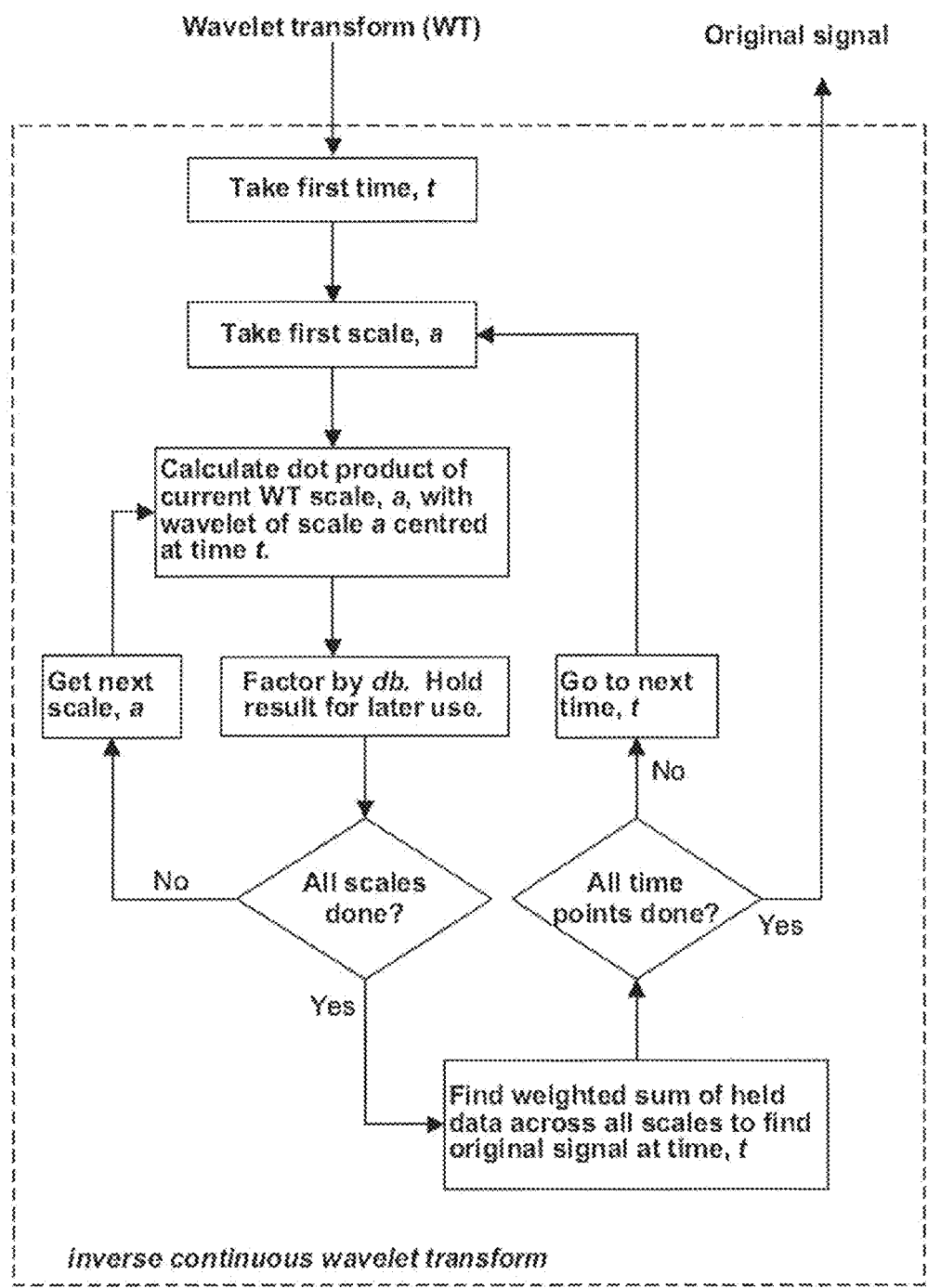
FIGS. 3(e) and 3(f) are flow charts of illustrative steps involved in performing an inverse continuous wavelet transform in accordance with an embodiment.
Figure 3F:
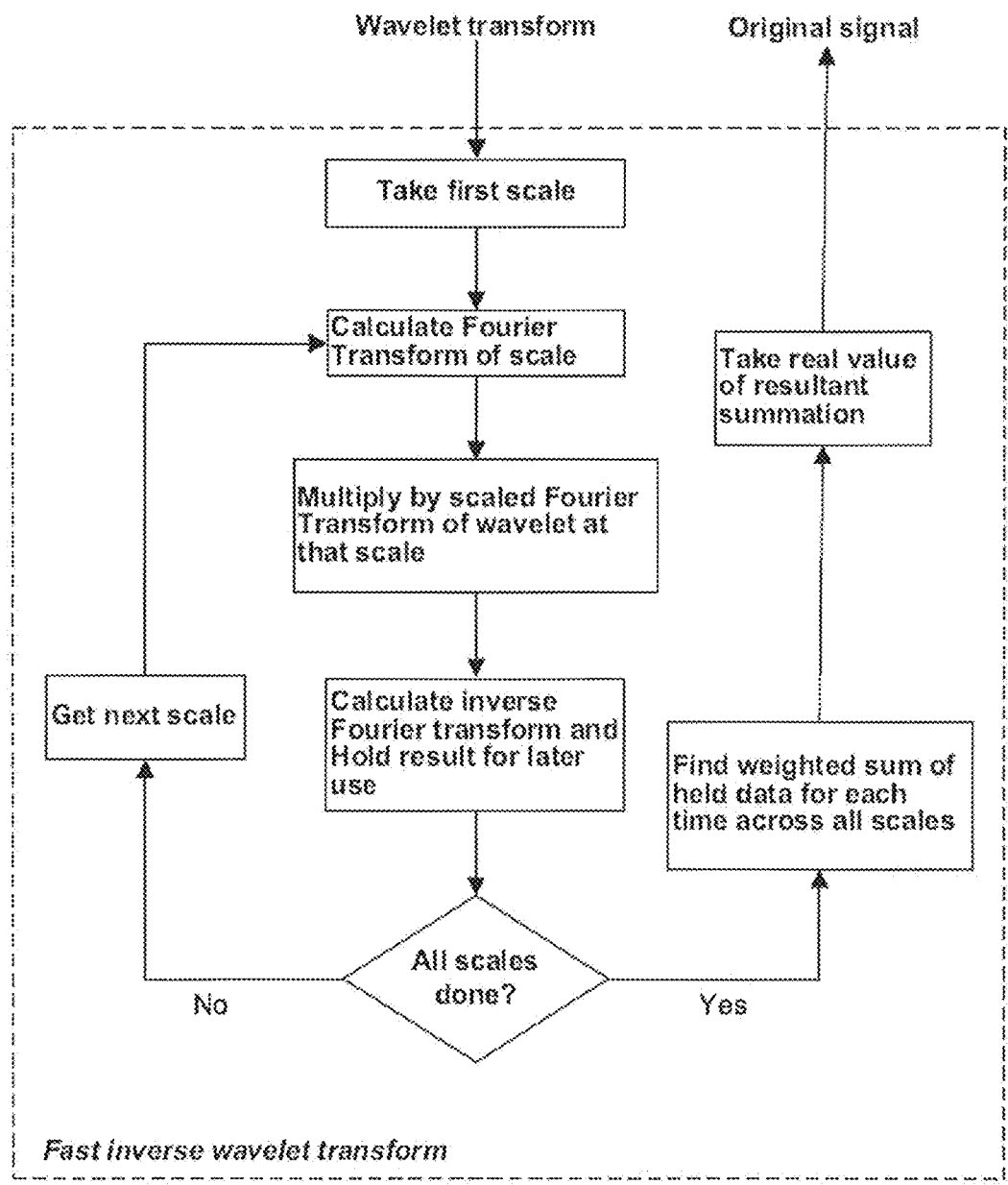

FIG. 3(e) is a flow chart of illustrative steps that may be taken to perform an inverse continuous wavelet transform in accordance with the above discussion. An approximation to the inverse transform may be made by considering Eq. 20 to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for processing a signal using the above mentioned techniques in analyzing multiple scale bands in the scalogram of a signal in order to obtain information about a process represented by the signal. An analysis may be performed to identify multiple scale bands that are likely to contain the information sought. Each scale band may be assessed to determine a band quality, and multiple bands may be combined based on the band quality. Information about the process may determined based on the combined band.

It will be understood that the present disclosure is applicable to any suitable signals and that physiological signals may be used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

The methods for determining physiological information from a signal in wavelet space described in this disclosure may be implemented on a multitude of different systems and apparatuses through the use of human-readable or machine-readable information. For example, the methods described herein may be implemented using machine-readable computer code and executed on a computer system that is capable of reading the computer code. An exemplary system that is capable of wavelet signal analysis is depicted in FIG. 4.

Figure 4:
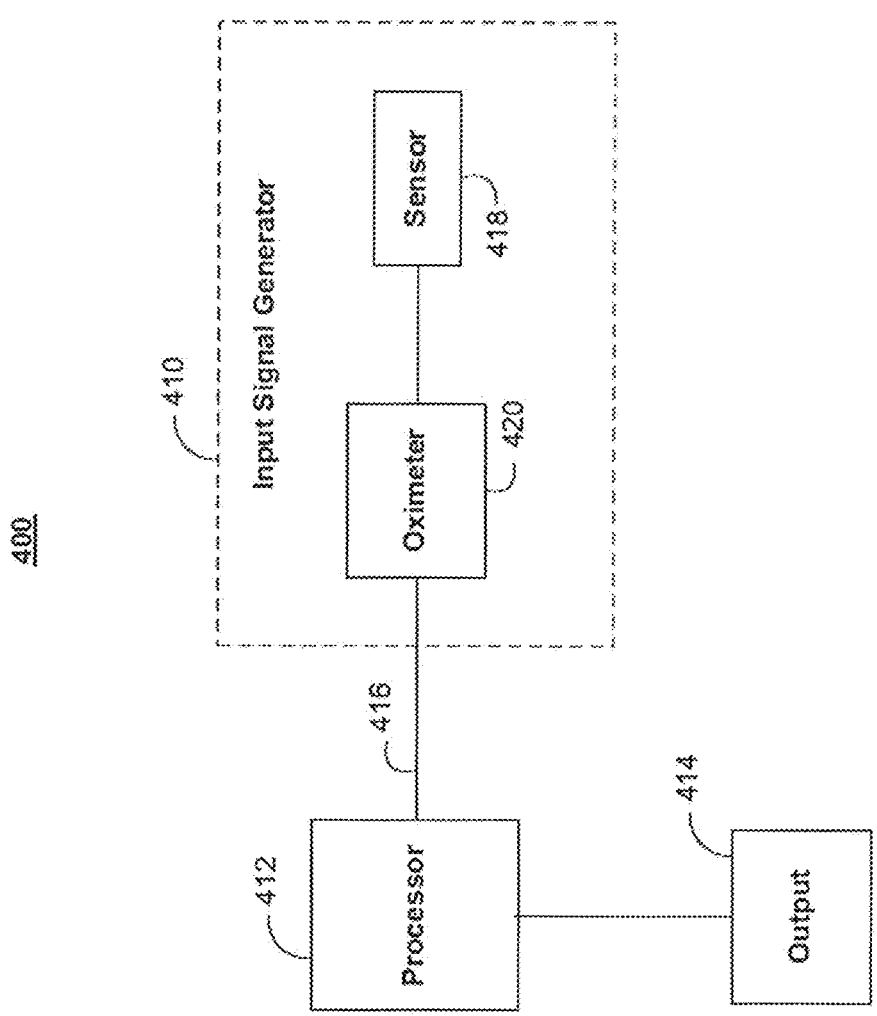
FIG. 4 is a block diagram of an illustrative continuous wavelet processing system in accordance with an embodiment.

FIG. 4 is a block diagram of an illustrative wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, hardware, and/or combinations thereof, for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram. The memory may be used by processor 412, to, for example, store any data related to any of the calculations described herein, including identifying scale bands, assessing band quality, combining scale bands, and determining physiological information, among others. This storage may take the form of any suitable data structure.

Processor 412 may be coupled to output 414. Output 414 may be any suitable output device such as one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5A:
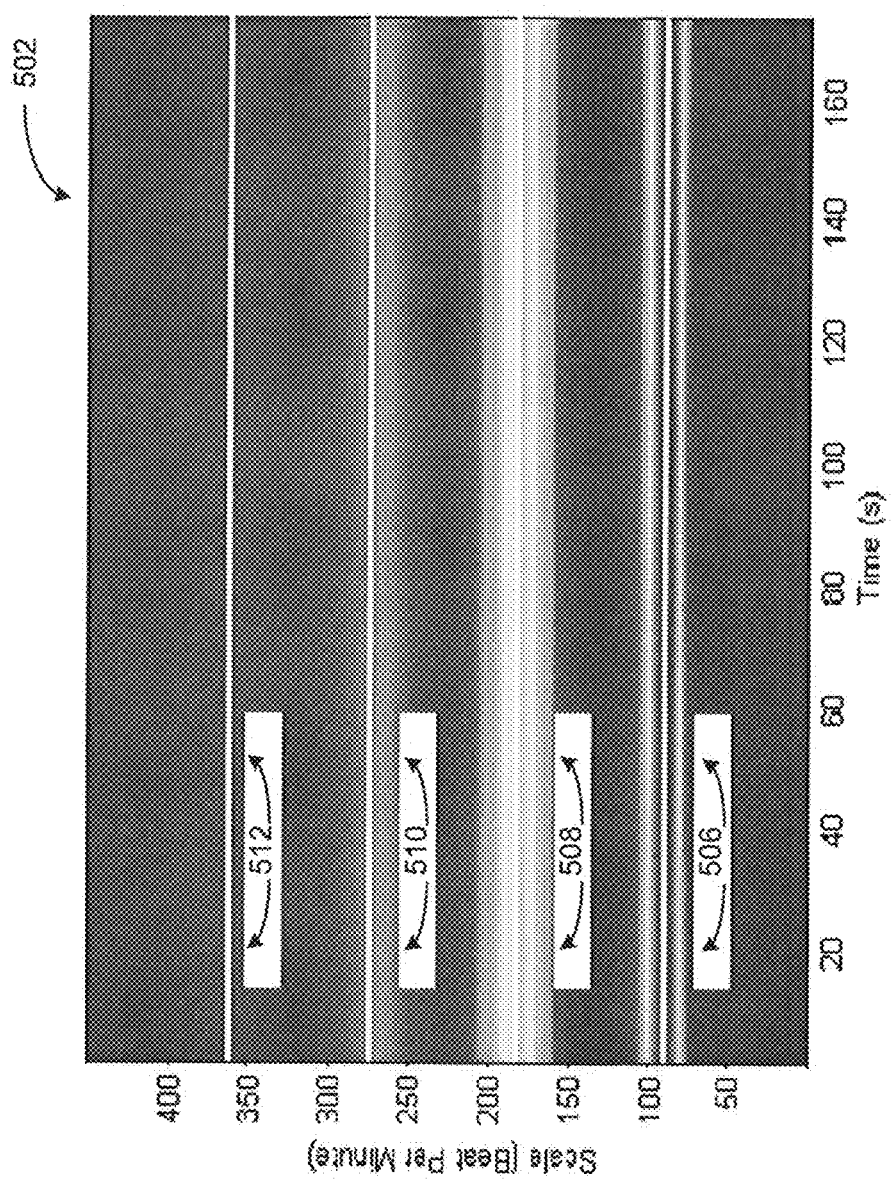
FIGS. 5(a) and 5(b) show illustrative views of scalograms representative of physiological processes in accordance with an embodiment.
Figure 5B:
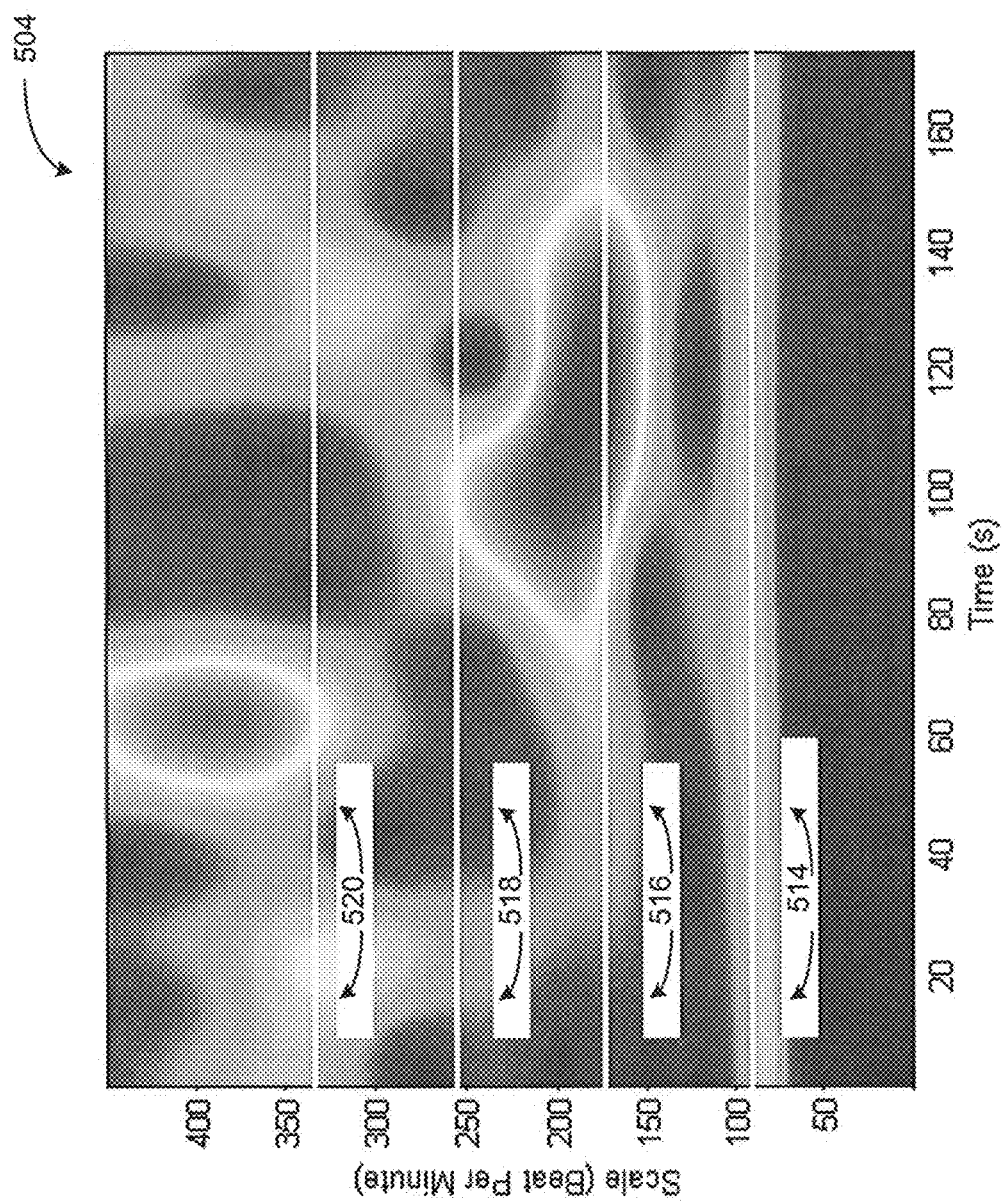
Figure 6:
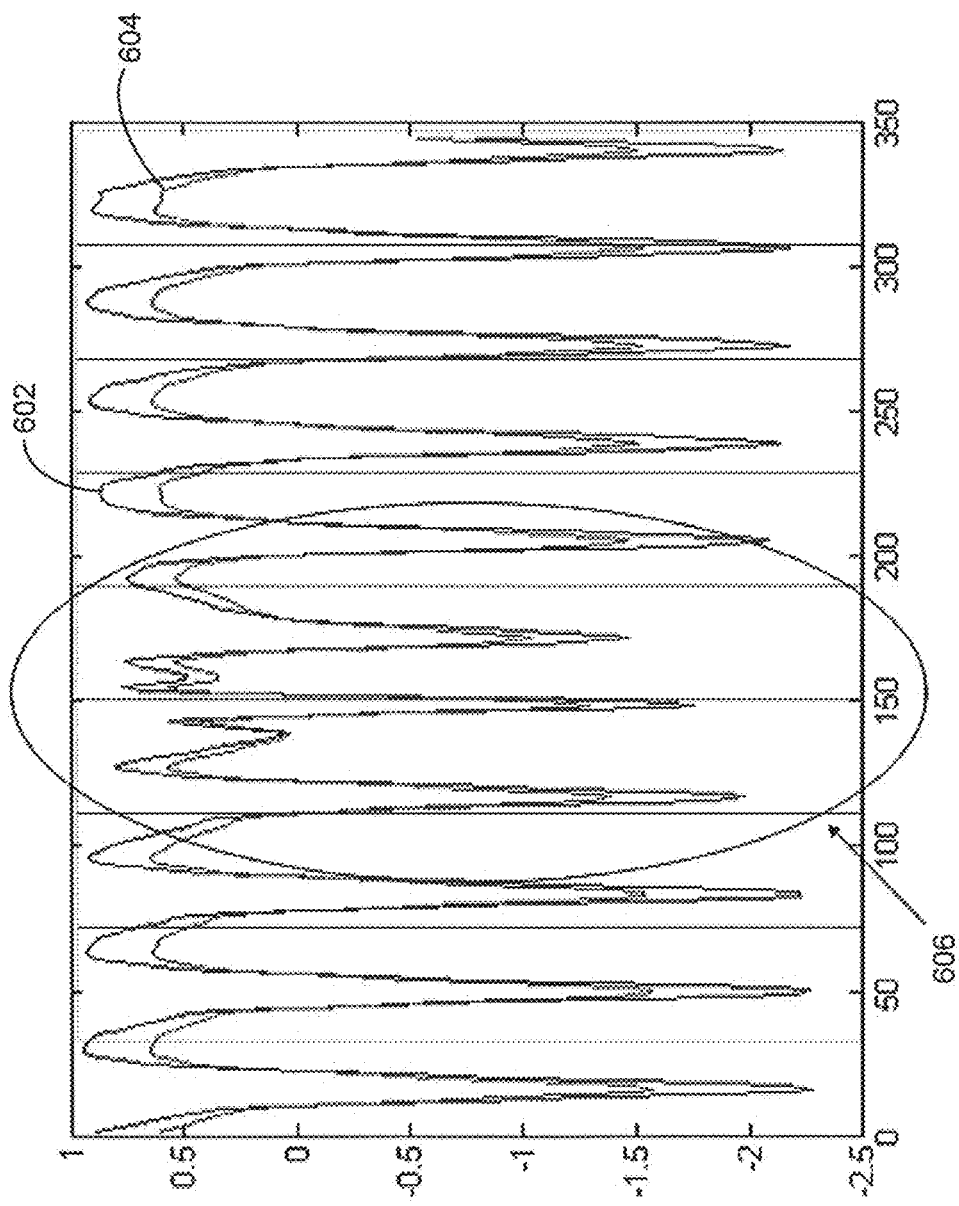
FIG. 6 depicts an illustrative time waveform representative of a physiological process in accordance with an embodiment.

The present disclosure provides techniques for determining information from representative signals by analyzing the signals in the wavelet domain, the time domain, and combinations of the two. In some embodiments, a signal may be analyzed in both domains in sequential steps, which may be performed in any suitable order. Examples of wavelet domain representations of signals are depicted in FIGS. 5(a) and 5(b), while time domain representations of signals are depicted in FIG. 6. These examples are discussed below and may illustrate the systems and methods that follow.

FIGS. 5(a) and 5(b) depict illustrative scalograms 502 and 504 of PPG signals that may be analyzed in accordance with an embodiment. Scalograms 502 and 504 may be generated and analyzed within system 10 of FIGS. 1 and 2 or system 400 of FIG. 4 as described above.

The PPG signal represented by scalogram 502 of FIG. 5(a) was measured from a patient in a relatively noise-free environment. Noise was then added to this PPG signal to produce the signal represented by scalogram 504 of FIG. 5(b). These two scalograms may be compared to illustrate several features, including several ways in which noise may introduce variation between scale bands within a wavelet domain representation of a signal.

Scalogram 502 may include first band 506 and related bands 508, 510 and 512. Related bands 508-512 may be located at scales that are approximately integer multiples of a scale associated with first band 506. In an embodiment, first band 506 may be a pulse band of a PPG signal and may be associated with a scale corresponding to a pulse rate. Scalogram 504 may include first band 514 and related bands 516, 518 and 520. Related bands 516-520 may be located at scales that are approximately integer multiples of a scale associated with first band 514. In an embodiment, first band 514 may be a pulse band of a PPG signal, and may correspond to first band 506 of scalogram 502. Bands 506-512 of scalogram 502 and bands 514-520 of scalogram 504 may be identified and analyzed for features that may communicate useful information about a physiological process reflected in the underlying PPG signals.

For example, scale bands 506-512 of scalogram 502 may be typical of scale bands that communicate information regarding a physiological process in a healthy patient under low-noise conditions. These scale bands 506-512 may be compared to corresponding scale bands 514-520 of scalogram 504. The PPG signal represented by scalogram 504 may have arisen, for example, from a patient experiencing low blood oxygen perfusion, resulting in a PPG signal that is obscured by other factors (e.g., hardware noise). One feature of scale bands 514-520 that suggests such an interpretation, for example, is the non-uniformity of the scalogram across each scale band and between scale bands. Techniques for assessing the quality of the scale bands with respect to information about an underlying physiological process are discussed in detail below.

FIG. 6 depicts illustrative time waveforms 602 and 604 derived from a PPG signal that may be analyzed in accordance with an embodiment. Time waveforms that may be analyzed by the methods described herein may be based directly on received signals such as input signal 416, or may be based on time waveforms arising from an inverse transformation of a signal in another domain. For example, a time domain signal may be generated by applying an inverse continuous wavelet transformation to a scalogram or a modified scalogram, as discussed above. Multiple time waveforms may arise from multiple components of a received signal (e.g., via input signal 416) and may be compared. For example, a received signal may include time waveform 602 based on a Red PPG signal and time waveform 604 based on an IR PPG signal An analysis of time waveforms 602 and 604 may be performed to determine information about a physiological process. In an embodiment, an analysis may identify one or more subwindows within at least one of time waveforms 602 and 604 that may be less suitable for use in determining physiological information. For example, an analysis may determine that the time waveforms 602 and 604 within the subwindows indicated by highlight region 606 are not sufficiently correlated. A patient monitoring system, such as system 10, may selectively discard or reduce the contribution of the time waveforms 602 and 604 within the subwindows indicated by highlight region 606. In an embodiment, time-domain signal processing techniques may be applied in conjunction with wavelet-domain signal processing techniques to determine information from a physiological signal. Examples of such embodiments, among others, will be discussed in detail below with reference to process 700 of FIG. 7.

Figure 7:
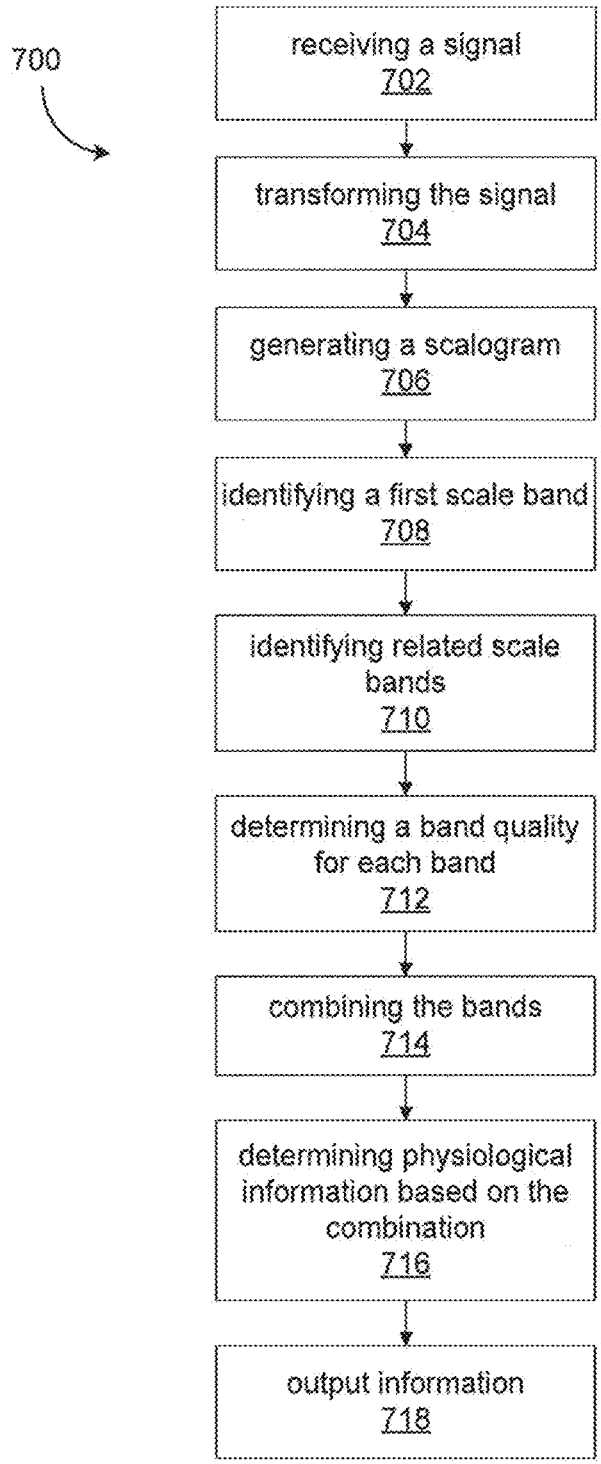
FIG. 7 is a flow chart of illustrative steps involved in determining physiological information from a physiological signal in accordance with an embodiment.

FIG. 7 is a flow chart of illustrative steps in a process 700 involved in determining physiological information in accordance with an embodiment. Process 700 may be performed by processor 412, or may be performed by any suitable processing device communicatively coupled to monitor 14. Process 700 may be performed by a digital processing device, or implemented in analog hardware.

Process 700 may be executed over a sliding window of a physiological signal. For example, process 700 may analyze the previous N samples of the physiological signal, or the samples of the physiological signal received in the previous T units of time. The length of the sliding window over which process 700 is executed may be fixed or dynamic. In an embodiment, the length of the sliding window may be based at least in part on the noise content of a physiological signal. For example, the length of the sliding window may increase with increasing noise. In an embodiment, the length of the sliding window over which process 700 is executed may be based at least in part on a patient condition. For example, the length of the sliding window may decrease when a patient is undergoing more rapid changes in physiological state.

It will be noted that the steps of process 700 may be performed in any suitable order, and certain steps may be omitted entirely, as will be discussed in additional detail below.

At step 702, a signal may be received. The signal (e.g., a PPG signal) may be received from any suitable source (e.g., patient 40) using any suitable technique. A received signal may be generated by sensor unit 12, which may itself include any of the number of physiological sensors described herein. The received signal may be signal 416, which may be generated by an oximeter 420 coupled between processor 412 and sensor 418. The received signal may include multiple signals, for example, in the form of a multi-dimensional vector signal or a frequency- or time-multiplexed signal. Additionally, the signal received at step 702 may be a derived signal generated internally to processor 412. Accordingly, the received signal may be a transformation of a signal 416, or may be a transformation of multiple such signals. For example, the received signal may be a ratio of two signals. The received signal may be based at least in part on past values of a signal, such as signal 416, which may be retrieved by processor 412 from a memory such as a buffer memory or RAM 54.

In an embodiment, the signal received in step 702 may be a PPG signal which may be obtained from sensor 12 that may be coupled to patient 40. The PPG signal may be obtained from input signal generator 410, which may include oximeter 420 coupled to sensor 418, which may provide a PPG signal as signal 416. In an embodiment, the PPG signal may be obtained from patient 40 using sensor 12 or input signal generator 410 in real time. In an embodiment, the PPG signal may have been stored in ROM 52, RAM 52, and/or QSM 72 (FIG. 2) in the past and may be accessed by microprocessor 48 within monitor 14 to be processed. Signal 416 may include one or more of a Red PPG signal component and an IR PPG signal component. Process 700 may be performed on an IR PPG signal component of a received signal, a Red PPG signal component of a received signal, or a combination thereof.

At step 704, the signal received at step 702 may be transformed. In an embodiment, processor 412 may transform the signal into any suitable domain, for example, a Fourier, wavelet, spectral, scale, time, time-spectral, time-scale domains, or any transform space. This transformation may be performed by any one or more of the transformation techniques described herein, including a continuous wavelet transformation. This transformation may be performed by any suitable processing device, such as processor 412, which may itself be a general-purpose computing device or a specialized processor. The transformation may also be performed by a separate, dedicated device. Processor 412 may further transform the original and/or transformed signals into any suitable domain. In an embodiment, step 704 is based at least in part on a continuous wavelet transformation. For example, a PPG signal may be transformed using a continuous wavelet transform as described above with reference to FIG. 3(*c*). In an embodiment, step 704 may include performing a continuous wavelet transform over the components of a PPG signal, including an IR PPG signal component, a Red PPG signal component, or any combination of components.

Any number of computational and/or optimization techniques may be performed in conjunction with the transformation of step 704. For example, if one or more scale bands associated with the physiological process of interest are approximately known or may be detected, the transformation may initially be executed only over scales at or close to these scale bands in order to reduce computation time. In an embodiment, if one or more scale bands communicate questionable or little information about the physiological process of interest, the transformation may not be executed over these scale bands. Any known information about the scale bands of interest may be stored in memory (e.g., ROM 52 or RAM 54). Such known information may be keyed to the characteristics of the patient, which may be input via user inputs 56 and used by monitor 14 to, for example, query a lookup table and retrieve the appropriate information. Additionally, any of the calculations and computations described herein may be optimized for a particular hardware implementation, which may involve implementing any one or more of a pipelining protocol, a distributed algorithm, a memory management algorithm, or any suitable optimization technique.

The transformation of the received signal at step 704 may also include pre- or post-processing transformations. These transformation may include any one or more of the following: compressing, multiplexing, modulating, up-sampling, down-sampling, smoothing, taking a median or other statistic of the received signal, removing erroneous regions of the received signal, or any combination thereof. In an embodiment, a normalization step is performed which divides the magnitude of the received signal by a value, which may be based on at least one of the maximum of the received signal, the minimum of the received signal and the mean of the received signal.

In an embodiment, at step 704, the signal may be filtered using any suitable filtering method. In an embodiment, a signal received at sensor 12 may be filtered by low pass filter 68 prior to undergoing additional processing at microprocessor 48 within patient monitoring system 10. The low pass filter 68 may selectively remove frequencies that may later be ignored by the transformation, which may advantageously reduce computational time and memory requirements. In an embodiment, the signal received in step 702 may be high or band pass filtered to remove certain frequencies. Such a filter may be a derivative filter. For example, a PPG signal may be filtered through a narrow band-pass filter that may be centered on the scale of a ridge of a scale band of interest. The PPG signal may be filtered through any suitable additional number and type of filters that may be centered on the scales of different ridges of interest. In an embodiment, the cutoff frequencies of a filter are chosen based on the frequency response of the hardware platform underlying patient monitoring system 10.

Different transformations may be applied to any one or more of the components of a signal, such as a Red PPG signal and an IR PPG signal. The transformation may be applied to a portion or portions of the received signal. The transformation of step 704 may be broken into one or more stages performed by one or more devices within wavelet processing system 400 (which may itself be a part of patient monitoring system 10). For example, a filtering operation may be applied by input signal generator 410 prior to passing the resulting signal 416 to processor 412, where it may undergo additional transformations. Embodiments of step 704 include any of the transformations described herein performed in any suitable order.

At step 706, a scalogram may be generated based on the transformed signal of step 704. Examples of such scalograms are depicted in FIGS. 3(*a*) and 3(*b*) and FIGS. 5(*a*) and 5(*b*). A scalogram may be generated by any of the techniques described herein, including those described above with reference to FIGS. 3(*a*) and 3(*b*). For example, processor 412 or microprocessor 48 may perform the calculations associated with the continuous wavelet transform of a signal and the derivation of the scalogram. As described above with reference to step 704, if one or more scale bands associated with the physiological process of interest are approximately known or may be detected, the scalogram may be generated only over scales at or close to these scale bands in order to reduce computation time. In an embodiment, if one or more scale bands communicate questionable or little information about the physiological process of interest, the scalogram may not be generated over these scale bands. In an embodiment, the scalogram generated in step 706 may be displayed for a user in any manner described herein, including via displays 20 and/or 28. The scalogram may also be recorded to a memory device (e.g., RAM 54 or a remote storage device) or a physical medium such as a print-out. In an embodiment, the scalogram generated at step 706 is based on any one or more features of the transformed signal of step 704. For example, the scalogram may represent the real part of a transformed signal, the imaginary part of a transformed signal, the modulus of a transformed signal, any other suitable feature of the transformed signal, or any combination thereof.

At step 708, a first scale band may be identified within the scalogram generated at step 706. The first scale band identified at step 708 may communicate information regarding a physiological process of interest. In an embodiment, the first scale band may be a scale band associated with the pulse rate and may communicate information regarding a patient's blood oxygen saturation.

A scale band may be characterized as a region of a particular size and shape used to analyze selected features in the domain space representation of signal 416. The selected features of a scalogram may communicate information about physiological processes and help to identify a first scale band. The selected features may be localized, repetitive, or continuous within one or more regions of the suitable domain space representation of a signal such as signal 416. For example, the selected features may be localized, repetitive, or continuous in scale or time within a wavelet transform surface. A region's size and shape may be selected based at least in part on the physiological process of interest. As an illustrative example, in order to analyze a patient's pulse band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. In an embodiment, the expected locations may be based at least in part on empirical data of a plurality of patients. The region may also be selected based at least in part on patient classification. For example, an adults pulse band location generally differs from the location of a neonatal patient's pulse band. Thus, the region selected for an adult may be different than the region selected for a neonate.

In some embodiments, a region may be selected based at least in part on features within a scalogram. For example, the scalogram may be analyzed to determine the location of a pulse band and its corresponding ridge. The pulse band ridge may be located using standard ridge detection techniques. In an embodiment, locating a ridge may include identifying locations (a*,b*) in a scalogram which satisfy the relationship $$\frac{\partial}{\partial a}\left(\frac{|T(a, b_\cdot)|^2}{a}\right)\bigg|_{a=a^*, b=b^*} = 0, \quad (23)$$

and locations in the vicinity of the ridge of Eq. 23. Such locations may be orthogonal to the ridge of Eq. 23, and may have lower values of the quantity $|T(a,b)|^2/a$. In an embodiment, locating a ridge may include identifying locations (a*, b) in a scalogram which satisfy the relationship $$\frac{\partial}{\partial a}(|T(a, b_\cdot)|^2)|^{a=a^*, b=b^*} = 0, \quad (24)$$

and locations in the vicinity of the ridge of Eq. 24. Such locations may be orthogonal to the ridge of Eq. 24 and may have lower values of the quantity $|T(a,b)|^2$.

Ridges may also be detected using the techniques described in U.S. patent application Ser. No. 12/245,326, filed Oct. 3, 2008, entitled "SYSTEMS AND METHODS FOR RIDGE SELECTION IN SCALOGRAMS OF SIGNALS," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, the region may be determined based at least in part on the repetitive nature of the selected features. For example, a band may have a periodic feature. The period of the feature may be used to determine bounds of the region in time and/or scale.

The region may be determined based at least in part on analysis of the physiological signal in another domain. For example, a patient's pulse rate may be determined by analyzing a PPG signal in the time domain. The region may be determined based at least in part on another received signal. For example, a patient's pulse rate may be determined manually by a care provider, or by any other pulse rate detection technique or device. This information may then be transmitted electronically or manually to a computational engine executing the calculations associated with step 708 and used to help localize the first scale band (e.g., via user inputs 56 or any suitable input or interface to monitor 14). Step 708 may involve the use of multiple sources of information from multiple patient monitoring signals to identify the first scale band, and may combine these sources of information in any suitable manner.

The size, shape, and location of the one or more regions may also be adaptively manipulated using signal analysis. The adaptation may be based at least in part on changing characteristics of the signal or features within the various domain spaces.

As a signal is being processed, for example by processor 412, the region may be moved over the signal in any suitable domain space over any suitable parameter in order to determine the value or change in value of the selected features. The processing may be performed in real-time or via a previously-recorded signal (stored, e.g., in RAM 54 or accessed from a remote device). For example, a region may move over the pulse band in the time-scale domain over time.

Once a first scale band is identified at step 708, at least one other scale band may be identified at step 710. The at least one other scale band may be related to the first scale band. The at least one other scale band may be related to the first band, for example, because of physiological phenomena such as internal reflections. The at least one other scale band may provide useful information regarding the physiological process by identifying physiologically-relevant features, improving the quality of the derived information, or a combination of the two. As an example, information regarding a patient's blood oxygen saturation is contained in the pulse band as discussed above with reference to step 708. Information about blood oxygen saturation is also contained in scale bands of the scalogram that are associated with integer multiples and near-integer multiples of the pulse rate. One will note that such related scale bands in a continuous wavelet transformation of a signal are not simply representative of harmonics of the pulse rate appearing in the signal (as would be the case in a Fourier transformation), but arise from correlated features within the signal. Thus, these related scale bands may be associated with scales that are not integer multiples of a pulse rate.

In an embodiment, step 710 includes distinguishing between related scale bands that carry information about a physiological process and related scale bands that arise from artifact and are thus less useful in determining physiological information. For example, when the first scale band is a pulse band, the scale band associated with half the pulse rate may not be included in the related scale bands identified in step 710 if it is determined that such a band stems from patient motion or a condition unrelated to the physiological process of interest.

In an embodiment, related scale bands may be associated with scales that are integer multiples of a first scale associated with the first scale band. For example, a pulse band in a scalogram may be associated with a scale corresponding to the pulse rate, and related bands may be associated with scales corresponding to twice the pulse rate scale, three times the pulse rate scale, etc. In some applications, related scale bands may be located by identifying other features within the scalogram, such as ridges or local maxima, which may occur at non-integer multiples of a first scale band. Any number of related scale bands may be identified, including integer-multiple, non-integer-multiple, or a combination of the two.

Any number of other scale bands may be identified at step 710. The number of scale bands identified may be fixed, or may be dynamic and based at least in part on patient and/or environmental conditions. For example, a related scale band may only be identified if a particular feature is present, such as an amplitude that exceeds a threshold. The identification of a scale band may be performed in conjunction with the assessment of scale band quality, as discussed further below with reference to step 712.

The location of the scale bands identified at steps 708 and 710 may be known in advance, identified dynamically, identified at predetermined intervals during a patient monitoring session, or any combination thereof. For example, the location of scale bands known to be relevant to a particular physiological process may be stored within a memory such as ROM 52 or RAM 54. In an embodiment, the location of the scale bands may be determined at regular intervals using any of the band location and detection techniques described herein. In an embodiment, the location of the scale bands identified at steps 708 and 710 may be determined based at least in part on the physiological signal. For example, a change in patient condition may trigger a re-determination of the location of the scale bands.

At step 712, a band quality may be determined for one or more of the bands identified at steps 708 and 710. As discussed above with reference to FIGS. 5(a) and 5(b), the amount of useful information about a physiological process of interest may vary between the identified scale bands. Certain types of noise and artifact may influence certain scale bands more than others, and such noise may reduce the amount of useful information that can be obtained from the band. For example, patient movement may distort the scale bands associated with lower scales, while certain types of hardware noise may distort the scale bands associated with higher scales. Assessing the quality of a scale band may involve determining an amount (relative or absolute) of useful information about the physiological process of interest contained in the scale band. Assessing the quality of a scale band may involve determining an amount of noise affecting the scale band.

Determining the quality of a scale band, as performed at step 712, may involve deriving a band quality metric. A band quality metric may provide a qualitative or quantitative measurement of the quality of the information contained in the scale band. The band quality metric may be a single value, or may be a waveform that varies in time, scale, or both. In an embodiment, step 712 involves using any one or more of the following metrics, in any combination, to determine the quality of a scale band.

1. Metrics based on scalogram energy. For example, a measure of the quality of a scale band may involve taking the ratio of the total energy of the scale band (or a portion of the scale band) and the total energy in a localized region of the scalogram (which may include the entire scalogram). In an embodiment, the energy in a region of the scalogram with boundary W may be calculated in accordance with $$\int_W \int \frac{|T(a,b)|^2}{a^2} da\, db. \tag{25}$$

This metric, and related metrics, may be analogous to a signal-to-noise (SNR) ratio, and any such commonly-used SNR metrics may be employed at step 712.

2. Metrics based on uniformity of scalogram features. These metrics may measure the consistency of features within each scale band, with greater consistency suggesting an absence of noise or corrupting interference. For example, the quality of a scale band may vary inversely or complementarily to the standard deviation of the amplitude of the scalogram within the scale band. The quality of a scale band may vary inversely or complementarily to any variability metric, including those based on the time derivatives of a portion or portions of the scalogram.

3. Metrics based on relative comparisons between scale bands. In an embodiment, the quality of a scale band is determined based at least in part on at least one other scale band. For example, the quality of a given scale band may be based at least in part on a comparison between an energy within the given scale band and a total energy across all identified scale bands. Such a comparison may take the form of a ratio, for example.

4. Metrics based on correlation between corresponding scale bands of received signals with multiple components. As discussed above, a received signal may include multiple components. For example, different components of the received signal may correspond to different frequencies, such as a Red PPG signal and an IR PPG signal. These components may each undergo steps similar to steps 704-710. These steps may be performed independently for each of the components, or may be dependent. At steps 708 and 710, scale bands may be identified in scalograms associated with each of the components. These scale bands may correspond to similar regions in the scalogram (e.g., scale ranges and temporal ranges), and thus may be compared between components. In one embodiment, a scale band associated with one component is correlated with a scale band associated with another component. In an embodiment, a quality metric may be based on the Pearson product moment correlation, and may be calculated in accordance with $$\frac{1}{T-1}\sum_{i=1}^{T}\left(\frac{x_i-\bar{x}}{s_x}\right)\left(\frac{y_i-\bar{y}}{s_y}\right), \quad (26)$$

where T is the number of samples or measurements; $x_i$ and $y_i$ are the ith measurements of signals x and y, respectively; $\bar{x}$ and $\bar{y}$ are the respective sample means; and $s_x$ and $s_y$ are the respective sample standard deviations. A correlation may be calculated in accordance with any known techniques, including those described in U.S. patent application Ser. No. 12/398,826, filed Mar. 5, 2009, entitled "SYSTEMS AND METHODS FOR MONITORING HEART RATE AND BLOOD PRESSURE CORRELATION," which is incorporated by reference herein in its entirety.

5. Metrics based on noise estimates. In an embodiment, determining a band quality may include assessing an amount of noise present in the band. Assessing an amount of noise may involve detecting a characteristic scalogram feature, such as a feature corresponding to the noise signature of a hardware device in the environment. Assessing an amount of noise may involve detecting an abnormality in features of the scalogram, such as those that arise in a PPG scalogram during patient movement. The amount of noise may be assessed by a quantitative or qualitative assessment, which may be used in an inverse or complementary relationship to a band quality assessment. In an embodiment, noise may be characterized by determining an energy in a region between two or more bands. This energy may itself serve as a noise measure, or may be used to determine a ratio of band energies that may serve as a noise measure. For example, noise may be measured by calculating a ratio of the energy of a region between two bands to the energy within one or both of the two bands. Noise may also be characterized by assessing the distribution of energy within one or more regions of a scalogram. For example, noise may be characterized by assessing the intermittency and/or entropy of an energy signal along a band or ridge. In an embodiment, noise may be characterized by comparing characteristics of a band or ridge with a theoretical model of the band or ridge. The theoretical model may represent a band or ridge in the absence of noise, and thus provide a point of comparison for a band or ridge based on actual patient data. Additional noise characterization techniques are described in a co-pending U.S. patent application of Addison et al., entitled "SYSTEMS AND METHODS FOR EVALUATING A PHYSIOLOGICAL CONDITION," Ser. No. 61/080,982, which is incorporated by reference herein in its entirety.

At step 714, at least two of the bands identified in steps 708 and 710 may be combined. For example, the bands may be summed together. In an embodiment the scalogram data included in each of the bands is concatenated across all bands to form a combined data set.

The combination of the identified bands may be based at least in part on the band quality or qualities determined at step 712. In an embodiment, the selection of points from each scale band to be included in a combined data set is made based on the band quality determined at step 712. In such an embodiment, more points may be included from scale bands of higher quality than from scale bands of lower quality. In an embodiment, the bands may be combined by performing a weighted summation, where the weighting of a particular scale band depends at least in part on the band quality. For example, a combined signal, $x_{total}$, may be calculated in accordance with $$x_{total} = \sum_{i=1}^{N} w_i x_i, \quad (27)$$

where N represents the total number of identified bands, $w_i$ represents the weight associated with band i and $x_i$ represents the scalogram values of band i. The weight $w_i$ may be calculated in any of a number of ways. In an embodiment, the weight $w_i$ is based on the fraction contained in band i of the total energy contained in all identified bands as described above. In an embodiment, the weight $w_i$ is a monotonic transformation of any of the band quality metrics described above with reference to step 712. The bands may also be combined via any suitable nonlinear combination, which may or may not include weights as described above.

In an embodiment, the combining of scale bands at step 714 may be performed for each component of a received signal with multiple components. For example, step 714 may result in a combined Red PPG band and a combined IR PPG band when the received signal has components including a Red PPG signal and an IR PPG signal.

In an embodiment, combining the scale bands at step 712 may include a threshold test on one or more of the band qualities. The threshold test may determine the degree to which a scale band should be included in a combination. Generally, a threshold test on a value may test any of a number of threshold conditions, including whether the value exceeds a single threshold, whether the value is below a single threshold, or whether the value falls within a specified range or ranges. The threshold test may be fixed, and retrieved by processor 412 from ROM 52 or RAM 54. The threshold test may be dynamic and depend, for example, on previously calculated scalograms, previously calculated band qualities, band qualities of more than one band, or any combination thereof. The threshold test may also depend on secondary signal quality indicators, such as an electromagnetic noise measuring device or a signal arising from sensor 418 indicating a malfunction or undesirable operating condition. In an embodiment, a band may be included in the combination if its associated band quality exceeds a threshold, and may not be included otherwise. In an embodiment, a band may be included in the combination with a first weight if an associated band quality exceeds a first threshold, and may be included in the combination with a second, higher weight if the associated band quality exceeds a second, higher threshold. These specific embodiments are illustrative, and appropriate threshold tests may include any number of threshold conditions and resulting implications for the band combination calculation.

In an embodiment of process 700, an analysis of one or more time waveforms may also be performed. Examples of such time waveforms are depicted in FIG. 6. In such an embodiment, received signals or transformations of received signals may be analyzed in the time domain to assess quality and/or noise. The signals examined in the time domain may be separately based on each of the bands identified in steps 708 and 710, or may be based on a combination of the bands (such as the combination resulting from step 714). As discussed above with reference to FIG. 6, an analysis of a time waveform may calculate a noise metric for one or more subwindows of a time window. The duration of a subwindow may be fixed, or may vary dynamically. In an embodiment, the duration of a subwindow of a time waveform containing information about a patient's pulse rate may depend upon the pulse rate. For example, each subwindow may corresponds to a single pulse, with durations that vary between subwindows to match the varying time between pulses. In an embodiment, subwindows of a time waveform may be removed from the data set or re-weighted based on a quality and/or noise assessment. For example, this assessment may be used in a threshold test as described above with reference to step 714. In an embodiment, at a particular time, the M best subwindows over a previous time interval will be retained for further analysis and the others discarded, based on a quality and/or noise assessment. In an embodiment, a quality and/or noise assessment may involve using analogs of any of the metrics described above with reference to determining scale band quality at step 712, including the following:

1. Metrics based on an energy of a time waveform. For example, a measure of the quality of a subwindow may involve taking the ratio of the total energy of the subwindow and the total energy in a portion of the window (which may include the entire window). This metric, and related metrics, may be analogous to a signal-to-noise (SNR) ratio, and any such commonly-used SNR metrics may be employed in an analysis of a time waveform.
2. Metrics based on uniformity of waveform features across subwindows.
3. Metrics based on relative comparisons between subwindows.
4. Metrics based on correlation between corresponding waveforms of received signals with multiple components.
5. Metrics based on noise estimates.
6. Metrics based on determined physiological information. In an embodiment, subwindows of a time waveform may be removed from the data set or re-weighted after an initial determination of physiological information from the combined scale bands. The determination of physiological information is discussed below with reference to step 716.

The analysis of a time waveform as described herein may be performed following any appropriate step of process 700 (e.g., after step 714 or iteratively with step 716) or may not be performed at all.

At step 716, physiological information may be determined based on the combining of scale bands at step 714. As described above, features of the scalogram may be representative of a variety of physiological processes. The physiological information determined at step 716 may be quantitative or qualitative, and may be the result of applying a predictive model such as a neural network to the combined signal (discussed in additional detail below). For example, the physiological information may be at least one of an identification of a medical condition of the patient and a current physiological measurement.

In an embodiment, the signal received at step 702 may be a signal with multiple components, such as a Red PPG signal and an IR PPG signal, and the first band identified at step 708 may be a pulse band. In such an embodiment, the combining step 714 may result in a Red combined band and an IR combined band, and the combined bands may be used to compute a blood oxygen saturation using any number of techniques. Several techniques that may be used to compute a blood oxygen saturation from a Red combined band and an IR combined band are described, for example, in U.S. patent application Ser. No. 10/547,430, filed Feb. 27, 2004, entitled "METHOD OF ANALYZING AND PROCESSING SIGNALS," which is incorporated by reference herein in its entirety.

At step 718, the physiological information determined at step 716 may be output. Physiological information may be output through a graphical representation, a quantitative representation, a qualitative representation, or combination of representations, via output 414 and may be controlled by processor 412. Output 414 may transmit physiological information by any means and through any format useful for informing a patient and a care provider of a patient status and may involve recording the physiological information to a storage medium. Quantitative or qualitative physiological information provided by output 414 may be displayed on a display, for example, on display 28. A graphical representation may be displayed in one, two, or more dimensions and may be fixed or change with time. A graphical representation may be further enhanced by changes in color, pattern, or any other visual representation. Output 414 may communicate the physiological information by performing at least one of the following: presenting a screen on a display; presenting a message on a display; producing a tone or sound; changing a color of a display or a light source; producing a vibration; and sending an electronic message. Output 414 may perform any of these actions in a device close to the patient, or at a mobile or remote monitoring device as described previously. In an embodiment, output 414 produces a continuous tone or beeping whose frequency changes in response to changes in a physiological process of interest. In an embodiment, output 414 produces a colored or flashing light which changes in response to changes in a physiological process of interest.

After or during the output of physiological information at step 718, the process 700 may begin again. Either a new signal may be received, or the physiological information determination may continue on another portion of the received signal(s). In an embodiment, processor 512 may continuously or periodically perform steps 702-718 and update the physiological information. The process may repeat indefinitely, until there is a command to stop the monitoring and/or until some detected event occurs that is designated to halt the monitoring process. For example, it may be desirable to halt a monitoring process when a detected noise has become too great, or when a patient has undergone a change in condition that can no longer be sufficiently well-monitored in a current configuration. In an embodiment, processor 412 performs process 700 at a prompt from a care provider via user inputs 56. In an embodiment, processor 412 performs process 700 at intervals that change according to patient status. For example, process 700 will be performed more often when a patient is undergoing rapid changes in physiological condition, and will be performed less often as the patient's condition stabilizes.

Several of the steps of process 700 may be aided by the use of a predictive model. For example, a predictive model may be employed in at least one of step 708 for identifying a first scale band, step 710 for identifying at least one related scale band, step 712 for determining a band quality, and step 714 for determining physiological information. In an embodiment, a predictive computational model may detect and characterize a noise or interference source affecting the received signal. In an embodiment, a predictive computational model determines estimates of a patient's current physiological status and prognosis as part of the determined physiological information. A predictive computational model executed, for example, by processor 412, may be based in part on at least one of the following data sources: the received signal (e.g., input signal 416); additional physiological signals; patient characteristics; historical data of the patient or other patients; and computational or statistical models of physiological processes. Processor 412 may retrieve any of these data sources from memory such as ROM 52 or RAM 54, from an external memory device, or from a remote device. The structure of a predictive computational model may, for example, be based on any of the following models: a neural network, a Bayesian classifier, and a clustering algorithm. In an embodiment, processor 412 develops a predictive neural network for noise assessment based at least in part on historical data from the given patient and/or other patients. In some embodiments, processor 412 implements the predictive computational model as a hypothesis test. Processor 412 may continually refine or augment the predictive computational model as new patient data and/or physiological signals are received. The predictive model may also be refined based on feedback from the patient or care provider received through the user inputs 56. Other predictive frameworks may include rule-based systems and adaptive rule-based systems such as propositional logic, predicate calculus, modal logic, non-monotonic logic and fuzzy logic.

It will also be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for processing a physiological signal, comprising:
   receiving, from a sensor, an electronic signal representative of a physiological process;
   using processor equipment for:
   transforming the electronic signal into a transformed signal based at least in part on a continuous wavelet transformation,
   generating a scalogram based at least in part on the transformed signal,
   identifying, within the scalogram, a first scale band associated with the physiological process,
   identifying, directly within the scalogram, a plurality of scale bands related to the first scale band,
   determining a band quality associated with each identified scale band,
   combining the identified scale bands based at least in part on the associated band qualities, and
   determining information regarding the physiological process based at least in part on the combining; and
   outputting the information to an output device.

2. The method of claim 1, wherein the first scale band comprises a region of the scalogram localized around a scale associated with a pulse rate.

3. The method of claim 2, wherein each of the plurality of scale bands comprises a region of the scalogram localized around a scale associated with a multiple of the pulse rate.

4. The method of claim 1, wherein determining a band quality associated with a scale band comprises comparing a total energy in the scale band with a total energy in a region of the scalogram.

5. The method of claim 1, wherein determining a band quality associated with a scale band comprises comparing a total energy in the scale band with a total energy in another scale band.

6. The method of claim 1, wherein determining a band quality associated with a scale band comprises evaluating the consistency of an amplitude of the scalogram within the scale band.

7. The method of claim 1, wherein combining the identified scale bands based at least in part on the associated band qualities comprises calculating a weighted combination of each of the scale bands, wherein the weight associated with a scale band is based at least in part on the associated band quality.

8. The method of claim 1, wherein combining the identified scale bands based at least in part on the associated band qualities comprises concatenating a portion of each of the scale bands, wherein the portion of a scale band is based at least in part on the associated band quality.

9. The method of claim 1, further comprising removing a portion of a scale band over a time interval based at least in part on a band quality over the time interval.

10. The method of claim 1, wherein transforming the electronic signal into a transformed signal comprises:
    calculating a first transformed signal from an electronic signal component associated with a first wavelength; and
    calculating a second transformed signal from an electronic signal component associated with a second wavelength.

11. The method of claim 10, wherein determining a band quality associated with a scale band comprises correlating a scale band within the first transformed signal with a corresponding scale band within the second transformed signal.

12. The method of claim 10, further comprising removing a portion of a scale band over a time interval based at least in part on a band quality over the time interval.

13. A system for processing a physiological signal, comprising:
    an output device, capable of receiving an electronic signal representative of information regarding a physiological process; and
    a processor, communicably coupled to the output device and capable of receiving an electronic signal representative of a physiological process, the processor being capable of:
    transforming the electronic signal representative of a physiological process into a transformed signal based at least in part on a continuous wavelet transformation,
    generating a scalogram based at least in part on the transformed signal,
    identifying, within the scalogram, a first scale band associated with the physiological process,
    identifying, directly within the scalogram, a plurality of scale bands related to the first scale band,
    determining a band quality associated with each identified scale band,
    combining the identified scale bands based at least in part on the associated band qualities,
    determining information regarding the physiological process based at least in part on the combining, and
    outputting an electronic signal representative of the information to the output device.

14. The system of claim 13, wherein the first scale band comprises a region of the scalogram localized around a scale associated with a pulse rate.

15. The system of claim 13, wherein combining the scale bands based at least in part on the associated band qualities comprises calculating a weighted combination of each of the scale bands, wherein the weight associated with a scale band is based at least in part on the associated band quality.

16. The system of claim 13, wherein transforming the electronic signal into a transformed signal comprises:

calculating a first transformed signal from an electronic signal component associated with a first wavelength; and calculating a second transformed signal from an electronic signal component associated with a second wavelength.

17. The system of claim 16, wherein determining a band quality associated with a scale band comprises correlating a scale band within the first transformed signal with a corresponding scale band within the second transformed signal.

18. Non-transitory computer-readable medium for use in processing a physiological signal, the non-transitory computer-readable medium having computer program instructions recorded thereon for:

transforming a signal representative of a physiological process into a transformed signal based at least in part on a continuous wavelet transformation, generating a scalogram based at least in part on the transformed signal, identifying, within the scalogram, a first scale band associated with the physiological process, identifying, directly within the scalogram, a plurality of scale bands related to the first scale band, determining a band quality associated with each identified scale band, combining the identified scale bands based at least in part on the associated band qualities, and determining information regarding the physiological process based at least in part on the combining.

19. The non-transitory computer-readable medium of claim 18, wherein the first scale band comprises a region of the scalogram localized around a scale associated with a pulse rate.

20. The non-transitory computer-readable medium of claim 18, wherein combining the scale bands based at least in part on the associated band qualities comprises calculating a weighted combination of each of the scale bands, wherein the weight associated with a scale band is based at least in part on the associated band quality.

* * * * *